United States Patent [19]

Braid

[11] 4,174,285
[45] Nov. 13, 1979

[54] LUBRICANT COMPOSITIONS AND ETHER OR ESTER OF 1-HYDROXYBENZOTRIAZOLE AS ANTIOXIDANT IN THE COMPOSITIONS

[75] Inventor: Milton Braid, Westmont, N.J.

[73] Assignee: Mobil Oil Corporation, New York, N.Y.

[21] Appl. No.: 939,763

[22] Filed: Sep. 5, 1978

[51] Int. Cl.$^2$ ............... C10M 1/20; C10M 1/32; C07D 249/18
[52] U.S. Cl. ............... 252/51.5 A; 252/51.5 R; 252/403; 548/259
[58] Field of Search ............... 252/51.5 A, 51.5 R, 252/403; 260/308 B

[56] References Cited

U.S. PATENT DOCUMENTS

| | | |
|---|---|---|
| 3,413,227 | 11/1968 | Howard et al. ............... 252/51.5 R |
| 3,597,353 | 8/1971 | Randell et al. ............... 252/50 |
| 3,788,993 | 1/1974 | Andress ............... 252/51.5 A |
| 3,791,803 | 2/1974 | Andress et al. ............... 44/63 |
| 4,048,082 | 9/1977 | Nnadi et al. ............... 252/51.5 A |
| 4,060,491 | 11/1977 | Bridger et al. ............... 252/50 |

FOREIGN PATENT DOCUMENTS 390092   1/1974   U.S.S.R. ............... 260/308 B

Primary Examiner—W. J. Shine
Attorney, Agent, or Firm—Charles A. Huggett; Raymond W. Barclay; Thomas S. Szatkowski

[57] ABSTRACT

Lubricant compositions containing oleaginous materials and, in amounts sufficient to impart antioxidation properties thereto, additives selected from the group consisting of ethers and esters of 1-hydroxybenzotriazole.

12 Claims, No Drawings

LUBRICANT COMPOSITIONS AND ETHER OR ESTER OF 1-HYDROXYBENZOTRIAZOLE AS ANTIOXIDANT IN THE COMPOSITIONS

BACKGROUND OF THE INVENTION

1. Field of the Invention

The invention relates to oleaginous compositions normally susceptible to oxidative deterioration. In particular, the invention relates to compositions such as mineral and synthetic lubricating oils, gear oils, transmission fluids, greases, and other oleaginous compositions normally requiring the presence of antioxidants.

2. Description of the Prior Art

Prior to the present invention, triazoles have been employed in lubricant compositions as metal deactivators. For example, U.S. Pat. No. 3,597,353 of Randell et al. discloses the use of 4,5,6,7-tetrahydrobenzotriazole as a metal deactivating additive for natural and synthetic lubricants. Similarly, U.S. Pat. No. 3,413,227 of Howard et al. teaches that an alkyl-substituted benzotriazole where the alkyl group contains from 2 to 20 carbon atoms can be used as a corrosion or tarnish inhibitor.

Bridger et al., in U.S. Pat. No. 4,060,491, discloses utilizing 5-alkyl benzotriazole, in which the alkyl group contains from 4 to 16 carbon atoms, in a method for reducing wear between moving steel-on-steel surfaces.

In U.S. Pat. No. 3,788,993 Andress, it is taught that benzotriazoles react with alkyl- or alkenylsuccinic anhydrides to form reaction products which impart corrosion inhibiting properties to lubricating oils.

Nnadi et al., in U.S. Pat. No. 4,048,082, discloses that esters of adducts of benzotriazole and unsaturated dicarboxylic acids or anhydrides thereof impart anti-rust properties to organic compositions.

None of the prior art patents disclose the ethers and esters of 1-hydroxybenzotriazole of the present invention.

SUMMARY OF THE INVENTION

It has now been found that ethers and esters of 1-hydroxybenzotriazole, having the formulae:

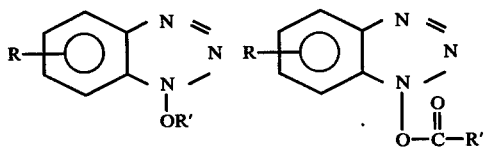

respectively, where

R is hydrogen or a hydrocarbyl group containing from 1 to about 12 carbon atoms, and R' is a hydrocarbyl group containing from 1 to about 16 carbon atoms impart antioxidant properties to the lubricant compositions to which they are added.

Referring to the above formulae, the preferred ethers and esters of 1-hydroxybenzotriazole and those in which R is hydrogen or an alkyl group containing from 1 to about 8 carbon atoms and R' is an alkyl, aryl, aralkyl or alkaryl group containing from about 1 to about 12 carbon atoms. Particularly preferred are those ethers and esters in which R is hydrogen or methyl and R' is an alkyl group containing from 1 to about 8 carbon atoms or an aralkyl group containing from 7 to about 12 carbon atoms.

The 1-hydroxybenzotriazole compounds which may be used to form the ethers and esters of the present invention have the formula:

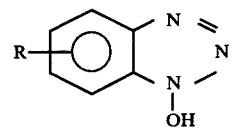

where R is hydrogen or hydrocarbyl containing from 1 to about 12 carbon atoms, and preferably is hydrogen or an alkyl group containing from 1 to about 8 carbon atoms. Particularly preferred are 1-hydroxybenzotriazole and 1-hydroxytoluotriazole.

In general, esters of 1-hydroxybenzotriazole are formed by reacting 1-hydroxybenzotriazole with an acyl halide or anhydride in proportions, expressed as molar ratios of benzotriazole compound to acyl halide or anhydride, of from 1:0.25 to about 1:4, with from about 1:0.5 to about 1:2 being preferred. Non-limiting examples of acyl halides and anhydrides which may be utilized to react with 1-hydroxybenzotriazole to form the esters of the present invention include: acetyl chloride, benzoyl chloride, pivolvyl chloride, acetic anhydride, propionic anhydride and butric anhydride. In addition, the esters of the present invention can be formed, in certain instances, by transesterfication of the 1-hydroxybenzotriazole with an alkyl ester. Non-limiting examples of alkyl esters which may be utilized for this purpose include: methyl acetate, ethyl hexanoate, methyl benzoate, methyl butyrate and methyl phenyl acetate.

The ethers of 1-hydroxybenzotriazole of the present invention are formed by reacting an alkali metal alcoholate of the 1-hydroxybenzotriazole with an alkyl or aralkyl halide with elimination of the corresponding alkali metal halide salt. The alkali metal alcoholate of 1-hydroxybenzotriazole is readily produced by known methods. Typical alkali metals which may be used include sodium or potassium. Non-limiting examples of alkyl or aralkyl halides which are reacted with the alkali metal alcoholate to form the ethers of the present invention include: 1-chlorooctane, 1-chlorobutane, 1-chlorohexane, benzylchloride and 1-chloro-3,3,4-trimethylpentane. The alkali metal alcoholate is reacted with the alkyl or aralkyl halides in proportions, expressed as molar ratios of alcoholate to halide, of from about 1:0.25 to about 1:4, with from about 1:0.5 to about 1:2 being preferred. The etherfication reaction may be conducted in a solvent medium such as N,N-dimethyl formamide, N,N-dimethyl acetamide or tert-butyl alcohol.

Temperatures from about 10° C. to about 150° C., with from about 20° C. to about 120° C. being preferred, are utilized for the esterfication or etherfication reactions. In general, the reactants are contacted for about 0.25 to about 20 hours, with from about 0.5 to about 6 hours being preferred. As those of skill in the art are aware, the particular reaction times utilized depend on the temperatures, and the reactants employed. Thus, at higher temperatures, the reaction time may be shorter than the time at lower temperatures, for a given pair of reactants.

Of particular significance, in accordance with the present invention, is the ability to improve the resistance to oxidation of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects any material which is normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenyl-ethers.

It is to be understood, however, that the compositions contemplated herein can also contain other materials. For example, corrosion inhibitors, extreme pressure agents, viscosity index agents, co-antioxidants, anti-wear agents and the like can be used. These materials do not detract from the value of the compositions of this invention, rather these materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2: RR 1005 on "Automatic Transmission Fluid/Power Transmission Fluid Property and Performance Definitions" Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

In general, the ethers and esters of 1-hydroxybenzotriazole of the present invention may be employed in any amount which is effective for imparting the desired degree of oxidation improvement or copper corrosion prevention. In many applications, however, they are effective employed in amounts from 0.01 to 10% by weight, and preferably from about 0.1 to 5% of the total weight of the composition.

DESCRIPTION OF SPECIFIC EMBODIMENTS

The following examples and comparative data will serve to illustrate the ethers and esters of 1-hydroxybenzotriazole of the present invention and the marked improvement in antioxidant properties of olegineous materials containing said adducts. It will be understood, however, that it is not intended that the invention be limited to the particular compositions containing those particular ethers and esters described herein. Various modifications of those materials and compositions can be employed, as will be readily apparent to those skilled in the art.

EXAMPLE 1

Pivalate Ester of 1-Hydroxybenzotriazole

To a mixture of 1-hydroxybenzotriazole (30.6 g), 1,2-dimethoxyethane (150 ml), and pyridine (16 g), there was added, while stirring at 21° C., pivaloyl chloride (24.1 g) during 0.75 hr. During the addition, the temperature of the reaction mixture was raised to 34° C. by the heat evolved. The reaction was then heated externally at 88° C. for an additional 0.5 hr. period then cooled, washed with water, and extracted with 1,1,2-trichlorotrifluoroethane. The extract was dried and stripped of solvent and the residue was column chromatographed on neutral alumina in benzene solvent. The product, 1-benzotriazolyl pivalate, was obtained as a brown oil after removal of the benzene solvent. The elemental analysis was as follows:

| Elemental Analysis, Wt. % |
|---|
| Anal. Calcined: C, 60.26 ; H, 5.98 ; N, 19.17. |
| Found: C, 60.36 ; H, 6.03 ; N, 19.9. |

EXAMPLE 2 n-Octyl 1-Benzotriazolyl Ether

A mixture of 1-hydroxybenzotriazole (30.6 g), N,N-dimethylformamide (150 ml), 1-chlorooctane (32.7 g) and potassium carbonate (50 g) was heated at 135° C. for 0.5 hr. while stirring. The reaction mixture was poured into water and the resulting mixture was extracted with benzene. The benzene extract was dried and stripped of solvent by rotary evaporation and distillation to a pot temperature of 100 C. at a pressure of less than 0.1 mm of mercury. The product, n-octyl 1-benzotriazolyl ether was obtained as a clear yellow oil residue. The elemental analysis was as follows:

| Elemental Analysis, Wt. % | |
|---|---|
| Anal.: | C, 67.98 ; H, 8.56 ; N, 16.98. |
| Found: | C, 68.18 ; H, 8.51 ; N, 16.9 |

The ethers and esters of 1-hydroxybenzotriazole produced in the above examples were then tested for oxidation inhibition activity.

For the oxidation test, the products were blended into a neutral solvent refined mineral base oil having a viscosity at 100° F. of 130 SUS. The oils were then subjected to a stream of air at the rate of 5 liters per hour at a temperature of 325° F. for 40 hours in the presence of metals having pro-oxidant properties: iron, copper, lead and aluminum. The lead sample was weighed before and after the test, since lead is one of the metals more susceptible to corrosion by oxidation. The test measurements are: change in acidity or neutralization number as measured by ASTM D-974, change in kinematic viscosity at 210° F., lead loss in milligrams and sludge. Results of the test are presented in Table 1.

TABLE 1

| Catalytic Oxidation Test 325° F., 40 hours | | | | |
|---|---|---|---|---|
| Base oil | ΔNN | ΔKV | Pb Loss mg | Sludge |
| Base oil without additives | 17 | 334 | 66 | Heavy |
| Esters of Example 1 | | | | |
| Base oil + 1 wt. % ester | 13.5 | 187 | 9 | Mod. |
| Base oil + .5 wt. % ester | 22.5 | 278 | 75.1 | Mod. |
| Base oil + .25 wt. % ester | 16.9 | 183 | 38.4 | Mod. |
| Ether of Example 2 | | | | |
| Base oil + 2 wt. % ether | 1.5 | 168 | 136 | Mod. |
| Base oil + 1 wt. % ether | 18.3 | 327 | 10.7 | Heavy |
| Base oil + .5 wt. % ether | 23.3 | .261 | 508 | Heavy |

The oxidation test was repeated but at a temperature of 450° F for 40 hours and using a base oil consisting of a synthetic ester lubricant which is prepared by esterfication of technical grade pentaerythritol with a mixture of commercial monocarboxylic (valeric and pelargonic) acids. The results are presented in Table 2.

TABLE 2

| Catalytic Oxidation Test 450° F., 40 hours | | | | |
|---|---|---|---|---|
| Base Oil | ΔNN | ΔKV | Pb Lead Loss mg. | Sludge |
| Base oil without additives | 8.25 | 586 | 13.7 | Trace |
| Esters of Example 1 | | | | |
| Base oil + 2 wt. % ester | 1.59 | 385 | 1.1 | Trace |
| Base oil + 1 wt. % ester | 10.9 | 486 | 2.6 | Nil |
| Ether of Example 2 | | | | |
| Base oil + 2 wt. % ether | 6.03 | 2.45 | 0.2 | Nil |

As shown by the data presented in Tables 1 and 2, the oxidative stability of the base oil is markedly improved by the addition of the ethers or esters of 1-hydroxybenzotriazole of the present invention.

I claim:

1. A lubricant composition which comprises a lubricant, and in an amount effective to impart anti-oxidation properties thereto, an additive selected from the group consisting of ethers and esters of 1-hydroxybenzotriazole having the formula:

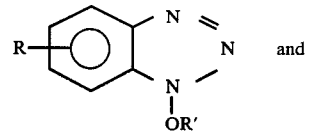

and

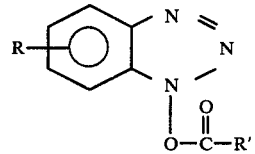

respectively, where
R is hydrogen or a hydrocarbyl group containing from 1 to about 12 carbon atoms, and
R' is a hydrocarbyl group containing from 1 to 16 carbon atoms.

2. The composition of claim 1 wherein R is hydrogen or an alkyl group containing from 1 to about 8 carbon atoms and R' is an alkyl, aryl, aralkyl or alkaryl group containing from about 1 to about 12 carbon atoms.

3. The composition of claim 1 wherein R is hydrogen or methyl and R' is an alkyl group containing from 1 to about 8 carbon atoms or an aralkyl group containing from 7 to about 12 carbon atoms.

4. The composition of claim 1 wherein said ether of 1-hydroxybenzotriazole is n-octyl 1-benzotriazolyl ether.

5. The composition of claim 1 wherein said ester of 1-hydroxybenzotriazole is the pivalate ester.

6. The composition of claim 1 wherein said lubricant is selected from the group consisting of mineral oils, synthetic oils and greases thereof.

7. The composition of claim 1 wherein said additive is present in an amount from about 0.01 to about 10% by weight of the total composition.

8. An ether or ester of 1-hydroxybenzotriazole compound having the formula:

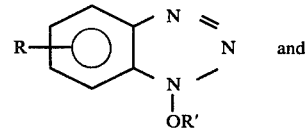

and

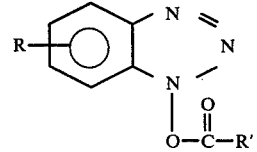

respectively, where
R is hydrogen or a hydrocarbyl group containing from 1 to about 12 carbon atoms, and R' is a hydrocarbyl group containing from 1 to 16 carbon atoms.

9. The compound of claim 7 wherein R is hydrogen or an alkyl group containing from 1 to about 8 carbon atoms and R' is an alkyl, aryl, aralkyl or alkaryl group containing from about 1 to about 12 1 carbon atoms.

10. The compound of claim 8 wherein R is hydrogen or methyl and R' is an alkyl group containing from 1 to about 8 carbon atoms or an aralkyl group containing from 7 to about 12 carbon atoms.

11. The compound of claim 8 wherein said ether is n-octyl 1-benzotriazolyl ether.

12. The compound of claim 8 wherein said ester is the pivalate ester.

* * * * *